United States Patent
Varela Macias

(10) Patent No.: US 12,427,233 B1
(45) Date of Patent: Sep. 30, 2025

(54) LACTATION ASSEMBLY

(71) Applicant: Carlos Xavier Varela Macias, San Sebastián (ES)

(72) Inventor: Carlos Xavier Varela Macias, San Sebastián (ES)

( * ) Notice: Subject to any disclaimer, the term of this patent is extended or adjusted under 35 U.S.C. 154(b) by 0 days.

(21) Appl. No.: 19/269,682

(22) Filed: Jul. 15, 2025

(51) Int. Cl.
*A61J 11/00* (2006.01)
*A61M 1/06* (2006.01)

(52) U.S. Cl.
CPC .............. *A61M 1/068* (2014.02); *A61J 11/00* (2013.01); *A61M 2205/3368* (2013.01); *A61M 2209/10* (2013.01)

(58) Field of Classification Search
CPC ........ A61M 1/06; A61M 1/062; A61M 1/068; A61M 2209/10; A61M 2205/3368; A61J 11/00; A61J 13/00; A61J 15/00; A61J 15/0003; A61J 15/0011
See application file for complete search history.

(56) References Cited

U.S. PATENT DOCUMENTS

| | | | | |
|---|---|---|---|---|
| 6,045,529 | A * | 4/2000 | Nuesch ................... | A61M 1/75 604/74 |
| 6,547,756 | B1 * | 4/2003 | Greter ............... | A61M 1/06935 604/74 |
| 7,641,629 | B2 * | 1/2010 | Yuen .................... | A61M 1/0697 604/74 |
| 8,167,833 | B2 * | 5/2012 | Tashiro .................. | A61M 1/06 604/74 |
| 8,900,182 | B2 * | 12/2014 | Britto ..................... | A61M 1/06 604/74 |
| 9,173,587 | B2 * | 11/2015 | Van Schijndel .. | A61M 1/06935 |
| 9,498,565 | B2 * | 11/2016 | Nowroozi ............... | A61M 1/06 |
| 9,539,376 | B2 * | 1/2017 | Makower ............ | A61M 1/0697 |
| 9,919,084 | B2 * | 3/2018 | Pollen .................. | A61M 1/067 |
| 10,016,566 | B2 * | 7/2018 | Zhang .................. | A61M 35/00 |
| 10,292,908 | B2 * | 5/2019 | Hyun .................. | A61J 15/0076 |
| 10,456,512 | B2 * | 10/2019 | Kim ....................... | A61M 1/062 |
| 10,483,002 | B2 * | 11/2019 | Guthrie ................ | G06F 3/0482 |
| 10,617,805 | B2 * | 4/2020 | Gaskin .................... | H04W 4/80 |
| 10,702,640 | B2 * | 7/2020 | Alvarez ............... | A61M 1/064 |
| 10,796,797 | B2 * | 10/2020 | Guthrie ............... | G06F 3/04847 |
| 10,857,271 | B2 * | 12/2020 | Bartlett ................. | A61M 1/062 |
| 2003/0188769 | A1 * | 10/2003 | Eisenberg ................ | B08B 9/32 134/152 |

(Continued)

*Primary Examiner* — Quynh-Nhu H. Vu
(74) *Attorney, Agent, or Firm* — Ruben Alcoba, ESQ

(57) ABSTRACT

A lactation assembly for improved functionality integrates breast milk expression, storage, feeding, and cleaning within a modular system. The assembly includes an assembly head with a touch screen, suction pump, and connectors, a milking module with a temperature-controlled milk container, a cleaning module for hygienic maintenance, a breast interface assembly for milk expression, and an oral interface assembly for feeding. Modular components connect via magnetic couplings and guide members for secure alignment. The system enables simultaneous or independent operation of expression and feeding, with transparent milk pathways for monitoring. Data on milk production, consumption, and temperature is stored and analyzed to recommend optimal expression and feeding times and ensure appropriate milk temperature. The portable, ergonomic design enhances user convenience while preserving milk quality and hygiene.

9 Claims, 11 Drawing Sheets

(56) References Cited

U.S. PATENT DOCUMENTS

| | | | |
|---|---|---|---|
| 2005/0101908 A1* | 5/2005 | Atkin | A61M 1/0693 604/74 |
| 2011/0192431 A1* | 8/2011 | Semans | B08B 3/04 134/166 R |
| 2015/0217033 A1* | 8/2015 | Pollen | A61M 1/062 604/74 |
| 2015/0352605 A1* | 12/2015 | Tiwari | B08B 3/10 134/105 |
| 2016/0030292 A1* | 2/2016 | Hyun | A23L 33/40 604/113 |
| 2017/0065753 A1* | 3/2017 | Nowroozi | A61M 1/06 |
| 2018/0126424 A1* | 5/2018 | Semans | B08B 3/02 |
| 2025/0249156 A1* | 8/2025 | Yi | A61N 1/0484 |

* cited by examiner

LACTATION ASSEMBLY

BACKGROUND

Breast milk extraction devices have been used since ancient times, initially employing rudimentary methods to express breast milk. Though primitive in comparison to modern technology, these devices represented early attempts to provide an alternative to manual lactation, laying the groundwork for future improvements in the field.

Over the years, breast pumps have evolved considerably, incorporating technological advancements that improved both efficiency and user comfort. Nevertheless, early versions exhibited limitations such as lack of portability, operational noise, discomfort during use, and a reliance on storing expressed milk for later use.

Modern breast pumps offer a combination of efficiency and convenience, enabling mothers to express milk quickly and effortlessly, providing the flexibility to feed infants breast milk even when direct breastfeeding is not possible. However, current devices typically require milk to be expressed, stored, and later fed to the infant, resulting in potential time inefficiencies and reduced opportunities for real-time mother-infant bonding.

Breastfeeding remains essential for the health and well-being of both mother and child. Persistent challenges associated with this natural practice have prompted the development of innovative solutions to facilitate and optimize the breastfeeding process.

Recognizing deficiencies in existing devices and the need for improved versatility and functionality, the lactation assembly disclosed herein has been developed to address these unmet needs.

SUMMARY

The present invention relates to a lactation assembly designed for improved functionality, convenience, and hygiene in the processes of breast milk expression, storage, feeding, and cleaning. The primary object of the invention is to provide a comprehensive, integrated, and user-friendly system that simplifies and optimizes lactation-related tasks while ensuring the safety, quality, and efficient management of expressed breast milk.

The lactation assembly comprises several modular components: an assembly head equipped with a touch screen, suction pump, control elements, hose connectors, and milk transfer tubes; a milking module containing a temperature-controlled milk container and a guided coupling system for secure attachment to the assembly head; a cleaning module for hygienically maintaining the breast and oral interface assemblies and system tubing; a breast interface assembly for milk expression; and an oral interface assembly for infant feeding.

The system allows for simultaneous or independent operation of the breast and oral interface assemblies, with seamless transport of expressed milk between modules via connected hoses and transfer tubes. The milking module not only stores expressed milk but maintains it at an optimal temperature for feeding. The cleaning module ensures sanitary conditions by circulating clean water through the system and collecting waste water separately.

The invention is further enhanced by a smart data management feature that stores and analyzes data on milk production, consumption, and temperature. This data is accessible via the assembly head's touch screen and enables the system to recommend optimal time windows for expressing and feeding, as well as ensuring milk is served at a suitable temperature for the infant.

Additional inventive aspects include: magnetic coupling and guide members for precise and secure alignment of modular connections; transparent components to visually track milk flow; an automatic redirect mechanism to return unconsumed milk to the container upon feeding cessation; and a portable and ergonomic design for ease of transport and use.

Through this integrated and intelligent design, the invention aims to improve the experience of both nursing parents and infants by streamlining the processes of expressing, storing, feeding, and cleaning breast milk while enhancing safety, hygiene, and usability. Technical overview of the disclosed lactation assembly:

The lactation assembly disclosed herein is a breast milk extraction and delivery device that efficiently expresses breast milk while also enabling immediate feeding without the need for interim storage. Additionally, it permits the storage of excess milk for subsequent use, offering a comprehensive and practical solution for lactation management. The device is configured to extract, store, and dispense milk simultaneously. However, it is a prerequisite that a quantity of milk be stored in the container prior to initiating the dispensing process.

The disclosed lactation assembly incorporates a milk heating system to maintain optimal feeding temperature, and features an automatic self-cleaning mechanism to ensure hygiene after use. It also integrates a data-linked informational interface, capable of monitoring and recording data associated with milk production, consumption, and temperature control.

This enables real-time monitoring of infant feeding patterns, prevention of unnecessary overproduction, and retrospective review of feeding schedules and quantities to optimize nutrition management tailored to the infant's needs.

In summary, the disclosed lactation assembly provides users with improved control and assurance regarding the breastfeeding process, offering data-driven guidance for determining optimal expression and feeding windows.

Key Functional Capabilities of the Disclosed Lactation Assembly:

The lactation assembly disclosed herein integrates five essential process functionalities: milk extraction and storage; simultaneous milk extraction, storage, and infant feeding; milk heating; automated self-cleaning; and data-linked informational interface.

Milk Extraction and Storage:

Conventional breast pumps, whether manual or electric, utilize suction to extract breast milk via a breast shield into a milk container. Manual pumps require user effort, while electric pumps are powered and often feature adjustable suction intensity and speed.

The disclosed lactation assembly comprises a milk module equipped with a suction control system utilizing a vacuum valve to generate negative pressure for extracting breast milk into a storage container through tubing. The system permits adjustment of suction intensity and frequency, enhancing user comfort and adaptability during the lactation process.

Simultaneous Extraction, Storage, and Infant Feeding:

A distinctive feature of the disclosed lactation assembly is its ability to perform milk extraction, storage, and delivery to the infant simultaneously, a capability that is not present in existing devices.

The milk module serves as an intermediate reservoir, allowing independent control of milk inflow and outflow via touchscreen interface commands. This system adapts in real-time to the needs of both mother and infant by enabling dynamic regulation of extraction rates and feeding flow, ensuring continuous, natural-paced feeding.

Transparent materials enable visual monitoring of the milk's movement through the system. When feeding ceases, the device detects the interruption and automatically retracts any remaining milk into the container, preventing drips and preserving milk for future use.

A high-strength magnetic coupling system ensures secure, stable alignment of system modules during operation.

Milk Heating Capability:

Breast milk is typically expressed at a body temperature of approximately 37° C. If not consumed immediately, it cools to room temperature or refrigerator storage levels. While bottle warmers and insulated containers exist to reheat stored milk, these solutions are designed for deferred feeding.

The disclosed lactation assembly includes a built-in heating mechanism to maintain optimal milk temperature directly prior to consumption. A flow meter is integrated to regulate flow and minimize air ingestion by the infant.

Automated Self-Cleaning:

The disclosed lactation assembly incorporates an automated cleaning system to maintain hygiene, especially in environments where immediate manual cleaning is impractical.

The cleaning module comprises a dual-chamber container for clean and waste water. Upon activation, clean water is circulated through the milk pathways and internal tubing, following the same route as the expressed milk. After cleaning, the water is collected in the waste compartment.

The system is designed to ensure comprehensive sanitation; all components are dishwasher-safe and can be fully disassembled for manual cleaning. Alignment features combined with the magnetic couplings ensure secure, intuitive module placement during reassembly.

Data-Linked Informational Interface:

The disclosed lactation assembly integrates an informational interface capable of monitoring and recording data regarding milk production, infant consumption, feeding durations, and milk temperature. This allows users to retrospectively review feeding histories and plan optimal expression and feeding schedules based on individualized infant needs.

This system provides enhanced control and reassurance in managing the breastfeeding process.

Summary of Innovations:

The disclosed lactation assembly incorporates the following novel systems: simultaneous milk extraction, storage, and infant feeding; integrated milk heating system; automated self-cleaning mechanism; data-linked informational interface; and modular magnetic coupling system for secure and intuitive module alignment.

BRIEF DESCRIPTION OF THE DRAWINGS

These and other features, aspects, and advantages of the present invention will become better understood with regards to the following description, appended claims, and drawings where:

DESCRIPTION

Figure 1:
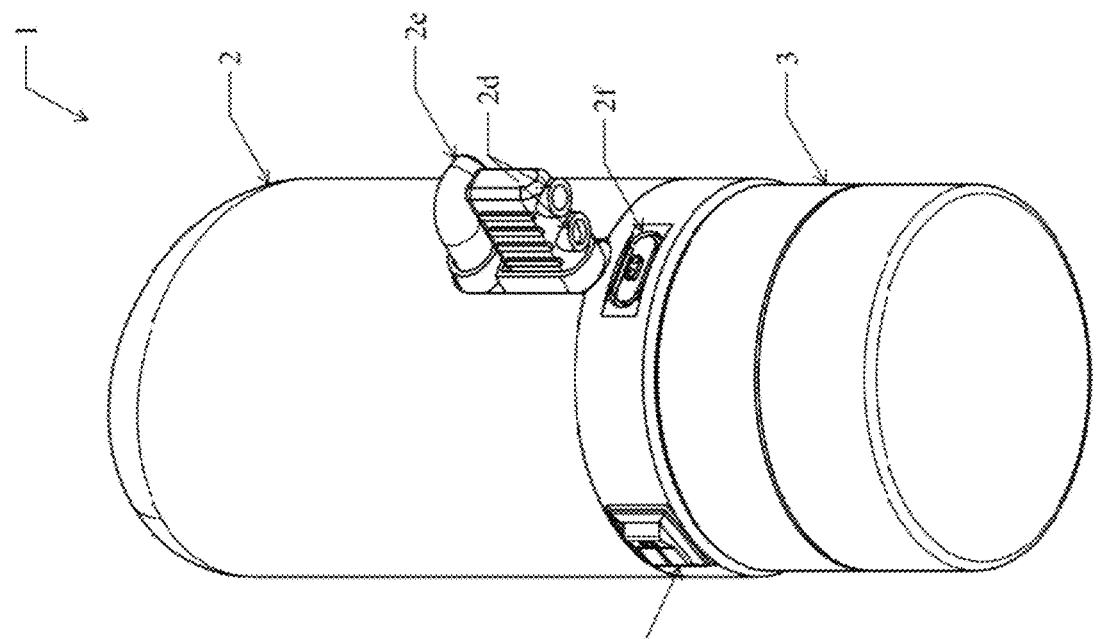
FIG. 1 is a perspective view of the lactation assembly with the milking module.
Figure 1:
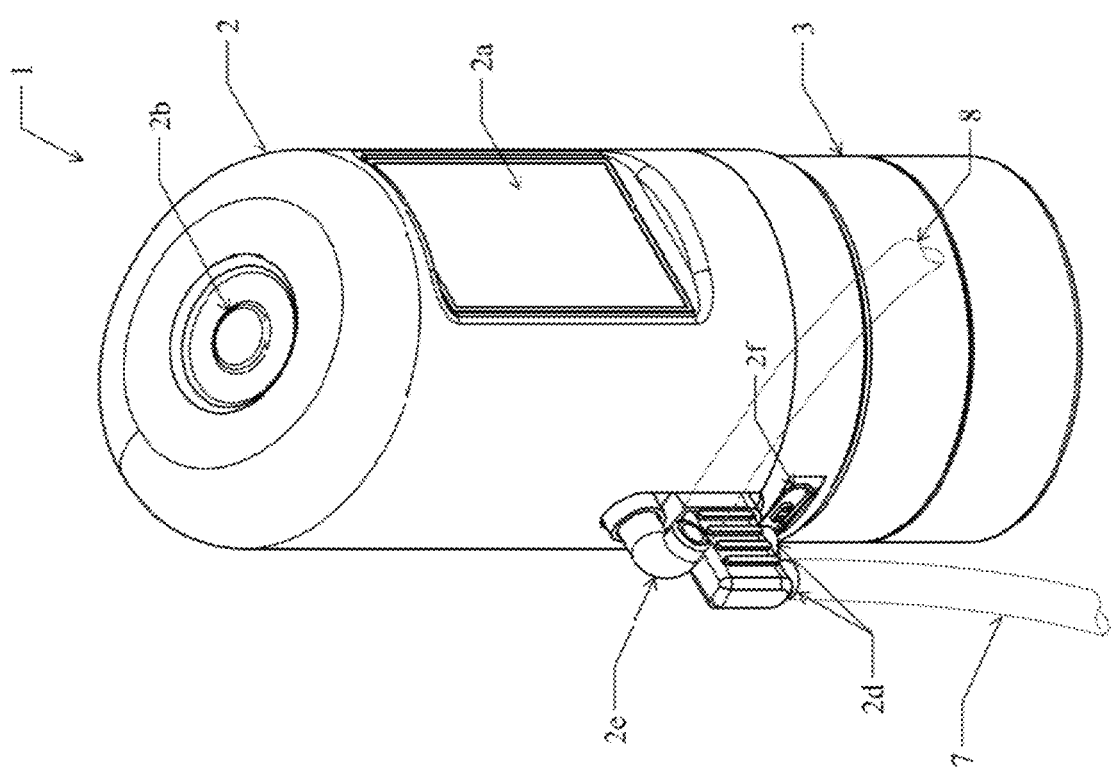
Figure 2:
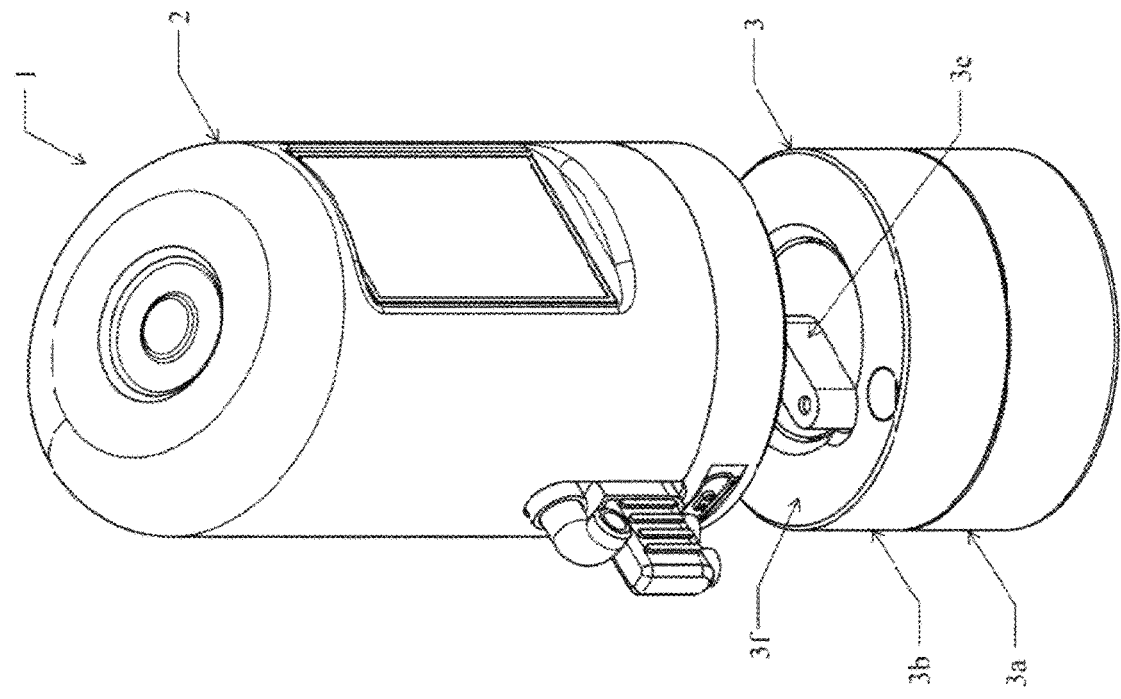
FIG. 2 is an exploded perspective view of the lactation assembly with the milking module.
Figure 2:
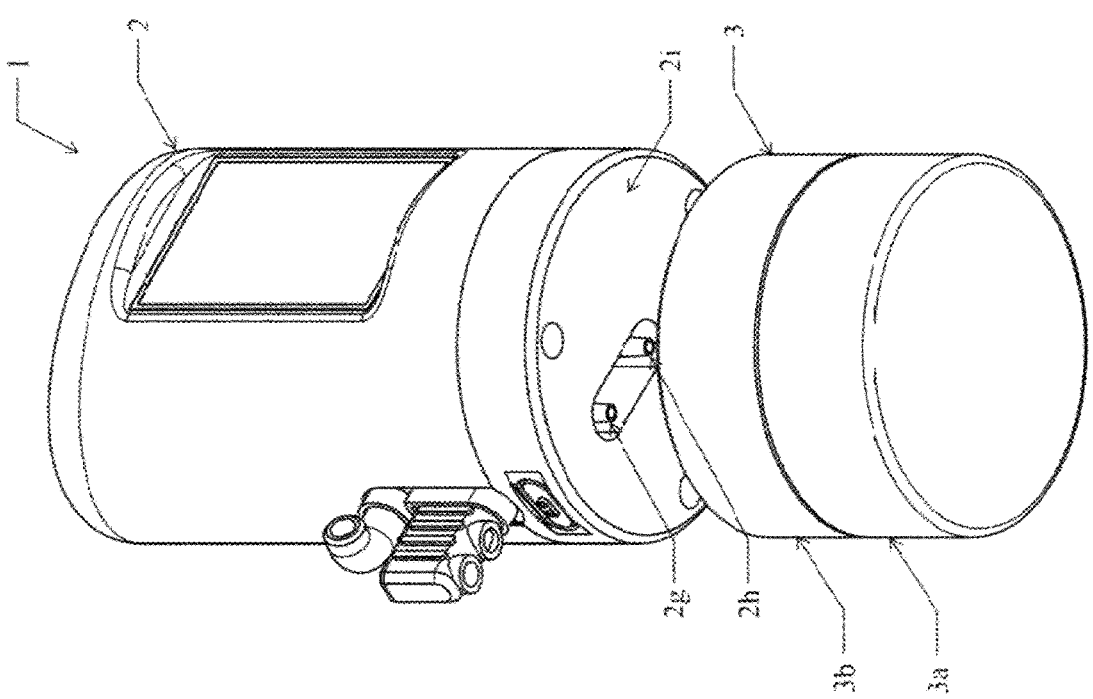
Figure 3:
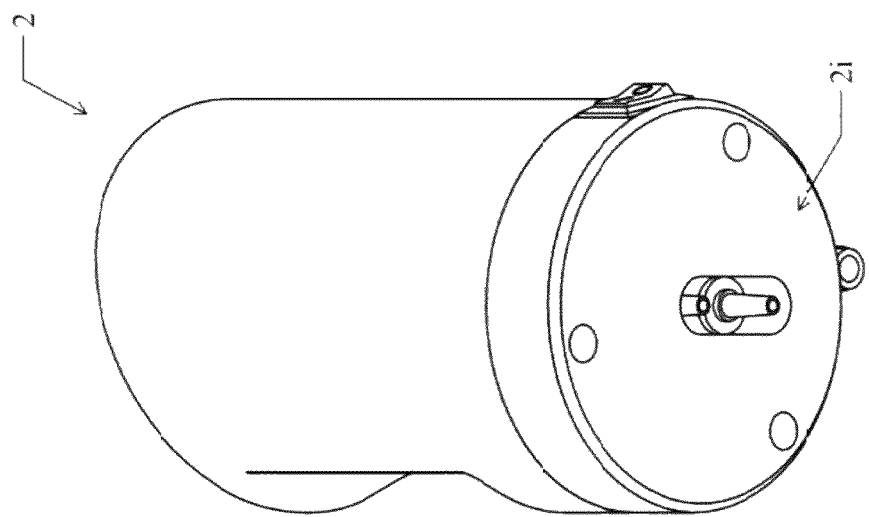
FIG. 3 is a perspective view of the assembly head.
Figure 3:
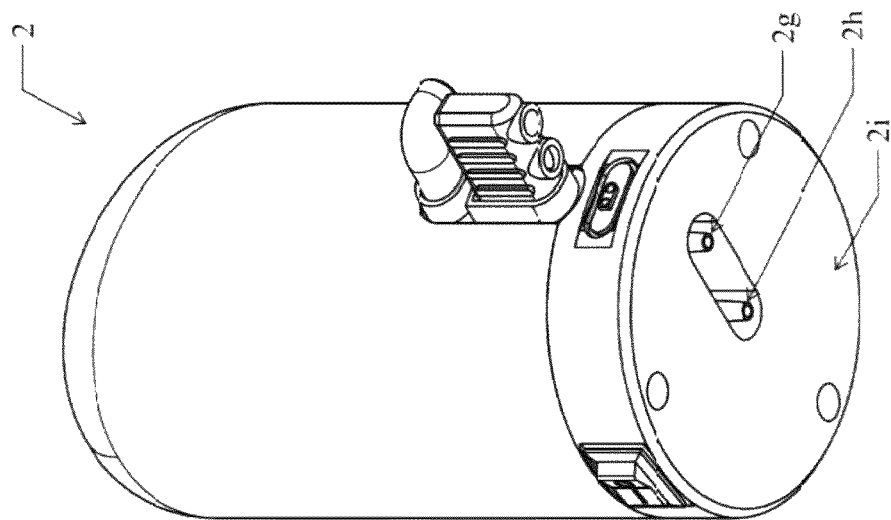
Figure 4:
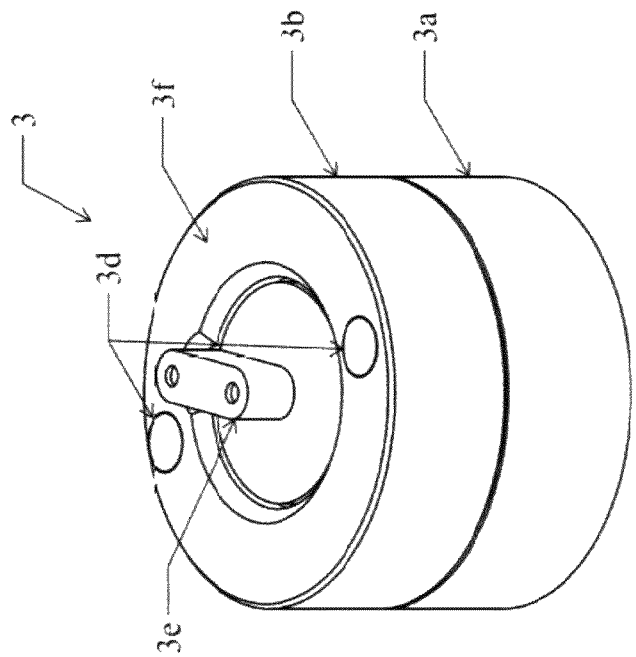
FIG. 4 is a perspective view of the milking module.
Figure 4:
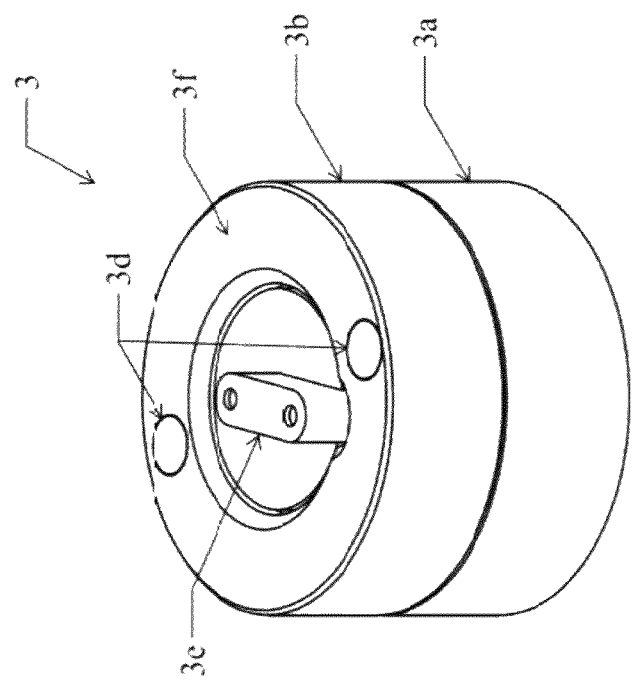
Figure 5:
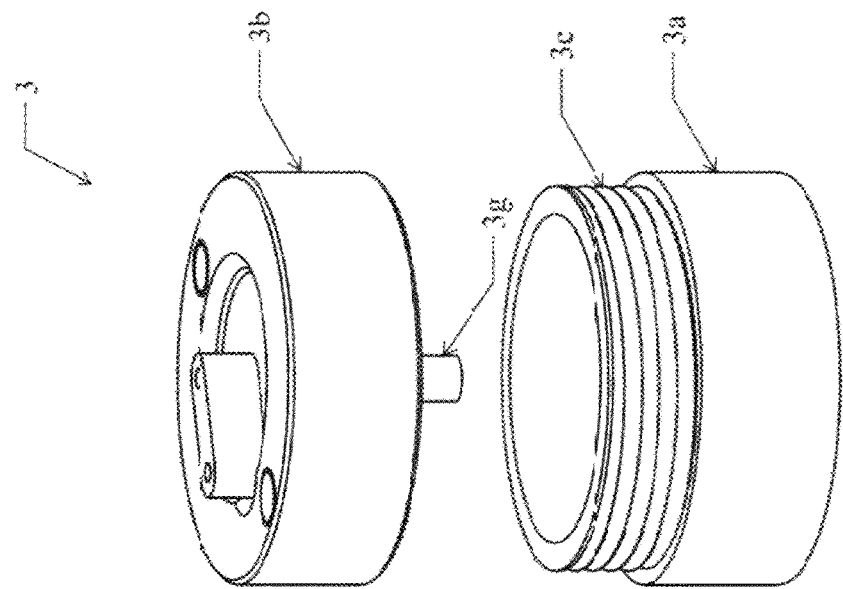
FIG. 5 is an exploded perspective view of the milking module.
Figure 5:
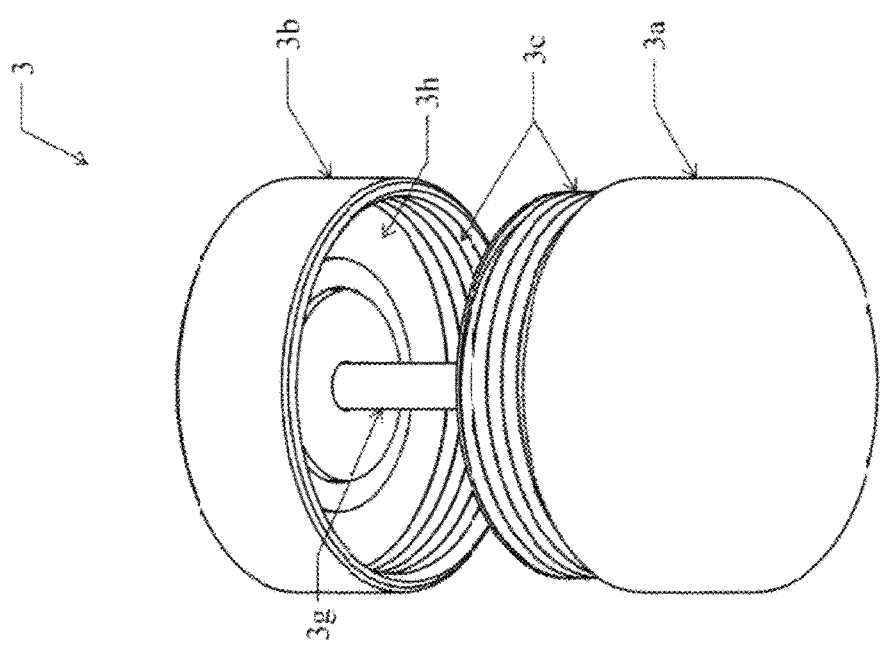
Figure 6:
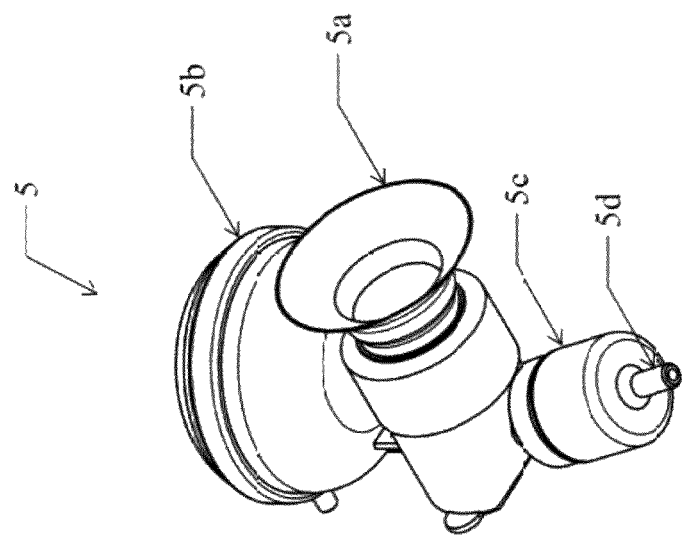
FIG. 6 is a perspective view of the breast interface assembly.
Figure 6:
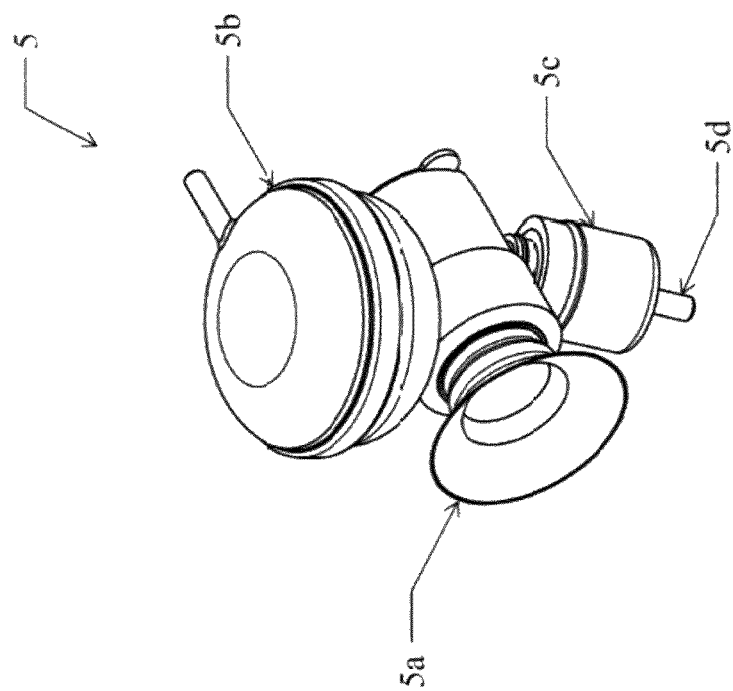
Figure 7:
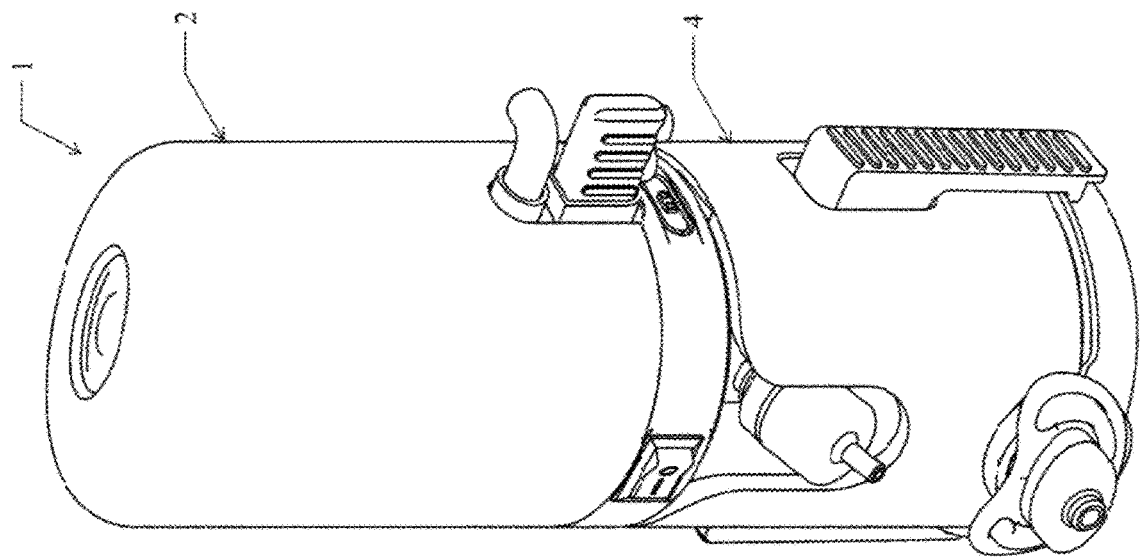
FIG. 7 is a perspective view of the lactation assembly with the cleaning module.
Figure 7:
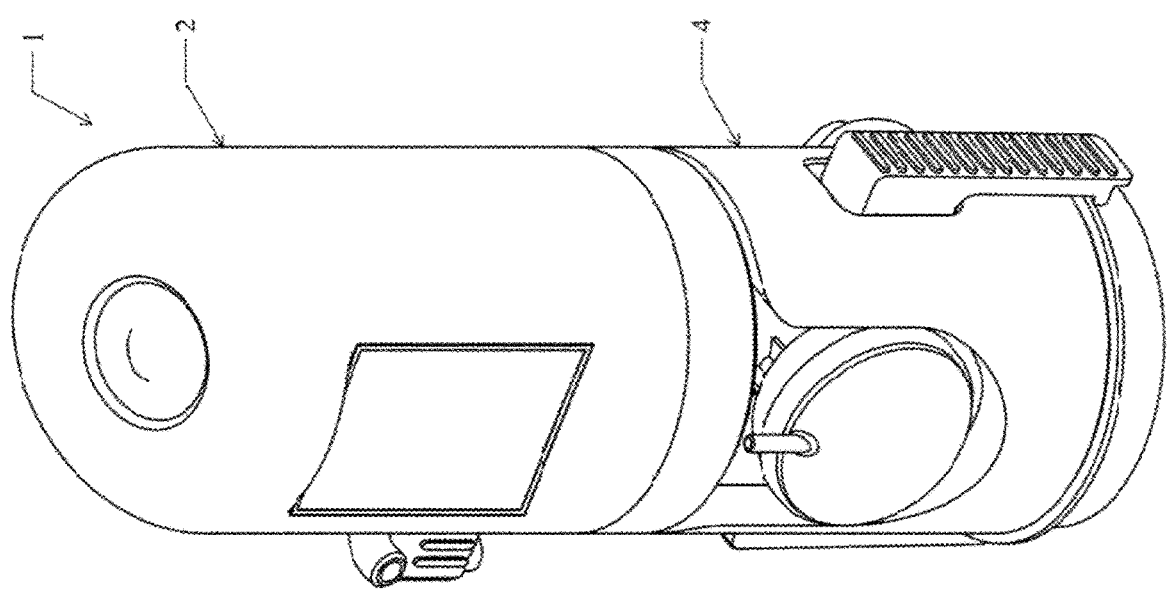
Figure 8:
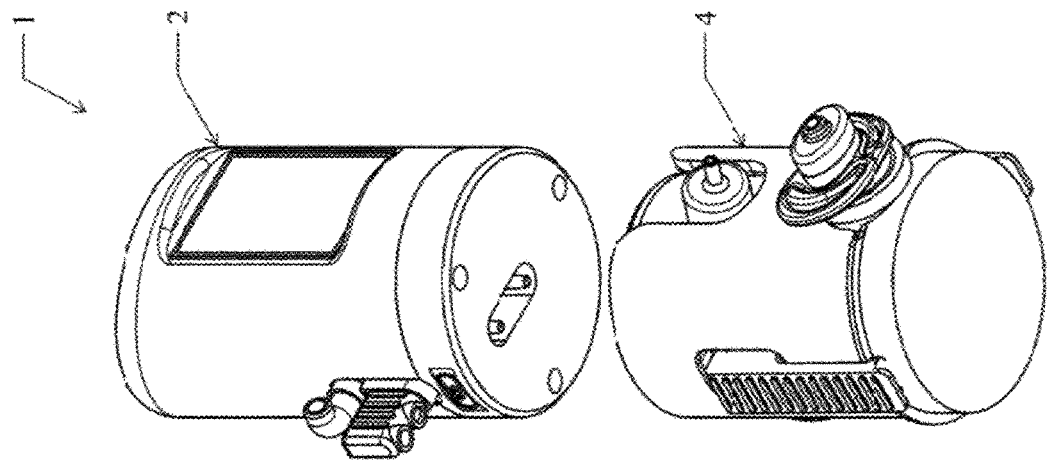
FIG. 8 is an exploded perspective view of the lactation assembly with the cleaning module.
Figure 8:
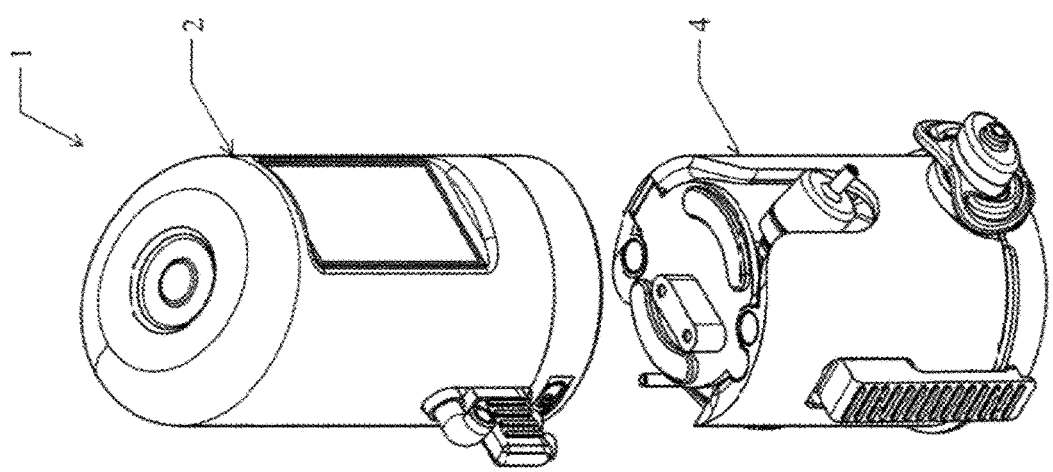
Figure 9:
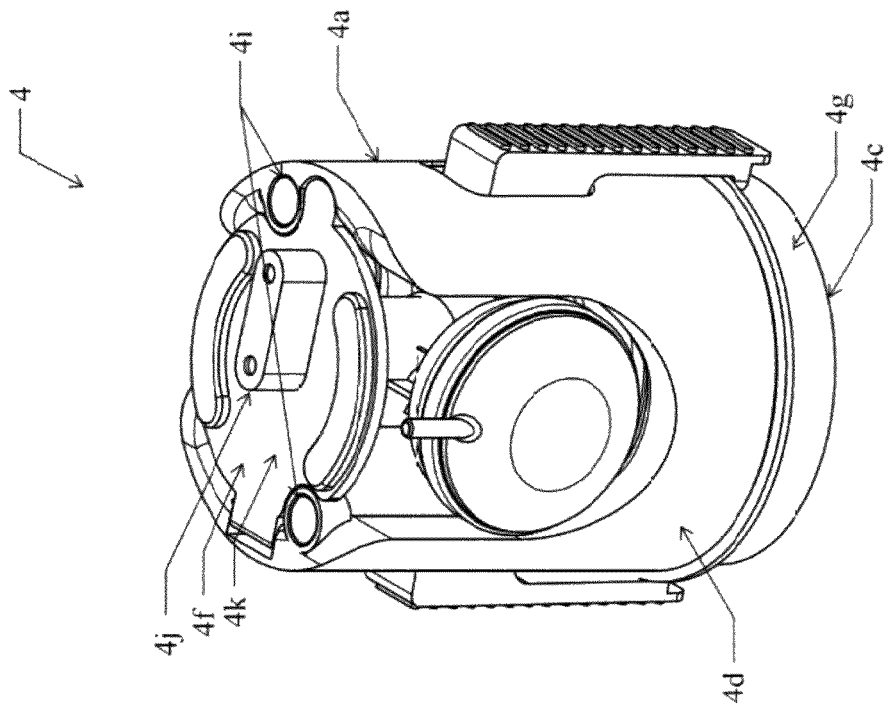
FIG. 9 is a perspective view of the cleaning module.
Figure 9:
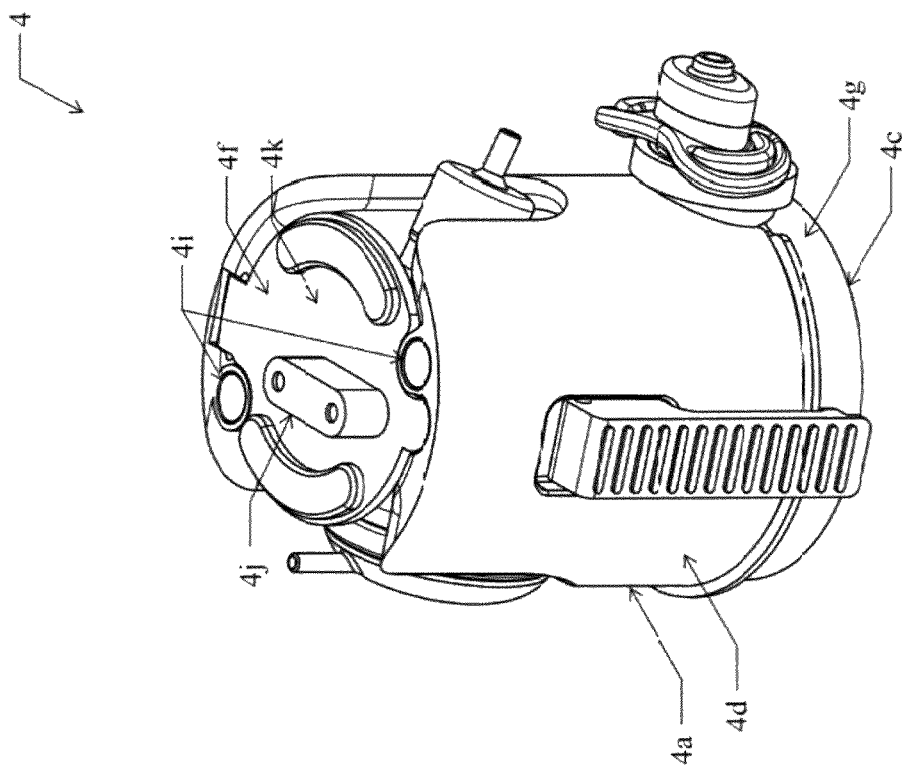
Figure 10:
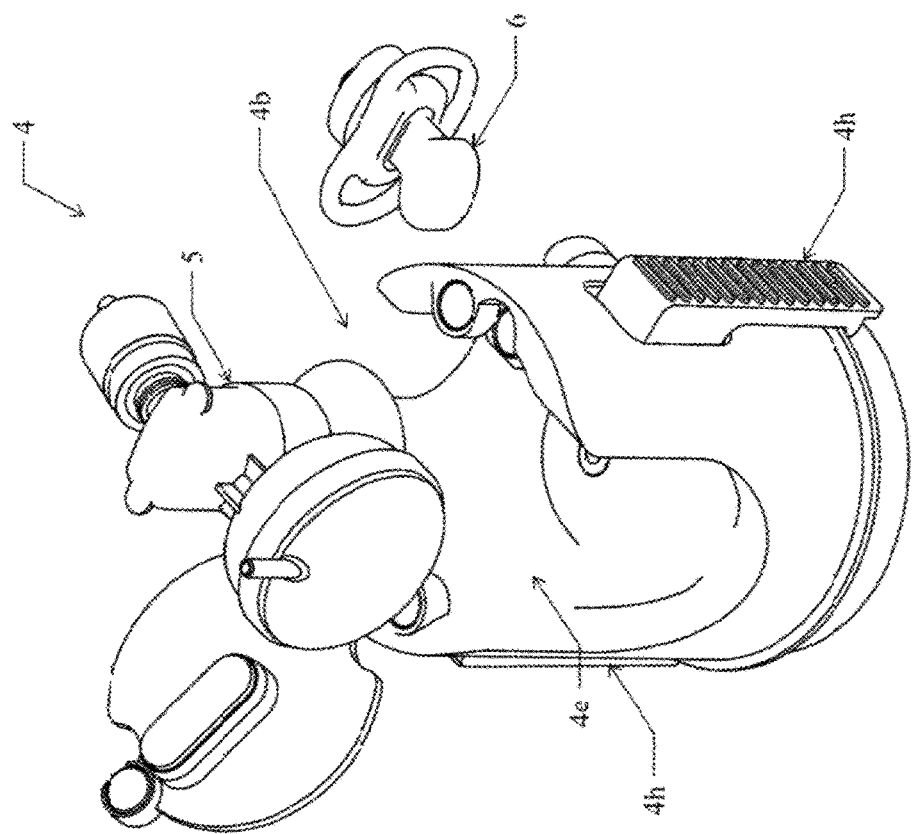
FIG. 10 is an exploded perspective view of the cleaning module.
Figure 10:
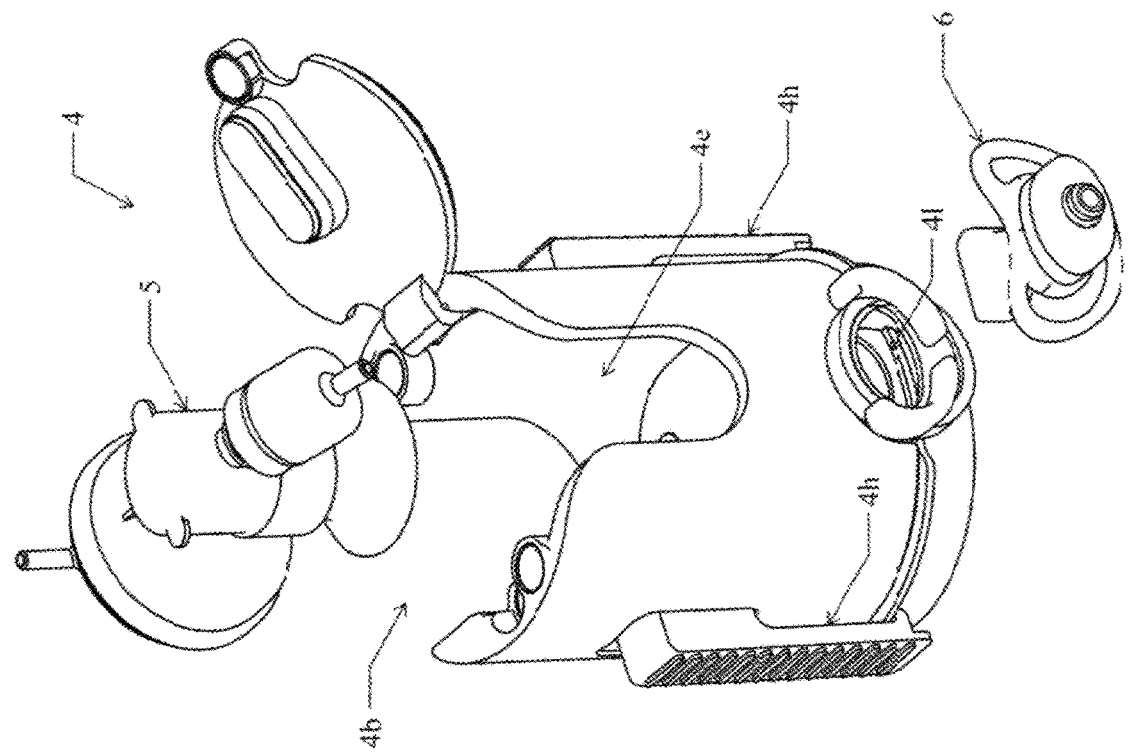
Figure 11:
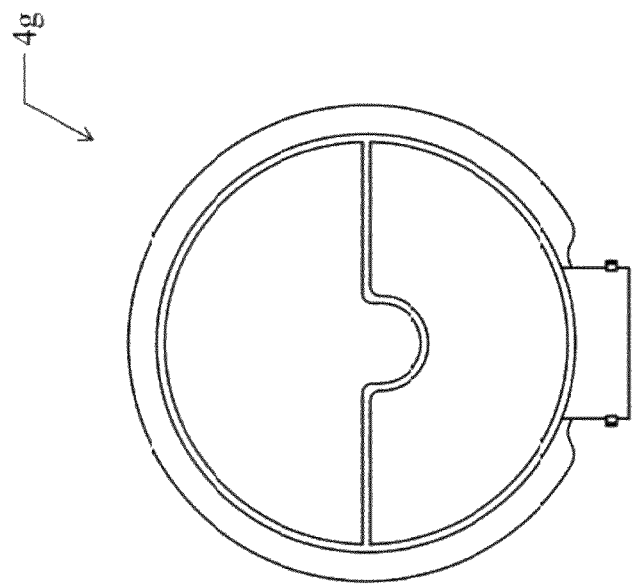
FIG. 11 is a perspective view of the water container.
Figure 11:
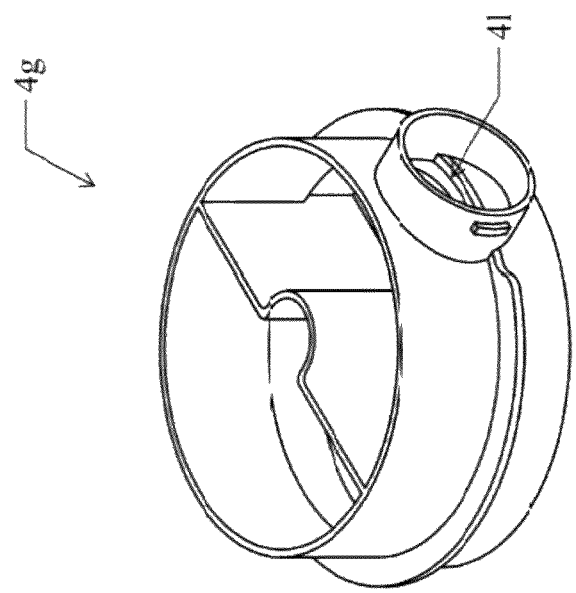

As seen in FIGS. 1-11, the present invention is a lactation assembly 1 for improved functionality. The lactation assembly 1 comprises an assembly head 2 with a touch screen 2a, a suction pump 2b, a user-actuatable control element 2c, at least one breast interface assembly hose connector 2d, an oral interface assembly hose connector 2e, a charging port 2f, a milk inlet tube 2g, and a milk outlet tube 2h, the milk inlet tube 2g and the milk outlet tube 2h extend to a lower connecting surface 2i of the assembly head 2. A milking module 3 with a milk container 3a configured to control the temperature of expressed breast milk contained therein, a milk container lid 3b that closes and seals the milk container 3a through a closure thread 3c, at least one milking module coupling magnet 3d and a milking module guide member 3e both placed on a first upper connecting surface 3f of the milk container lid 3b, and a milk transfer tube 3g that projects from a lower surface 3h of the milk container lid 3b. A cleaning module 4 with a body 4a that defines an upper opening 4b, a lower end 4c and a sidewall 4d that collectively define an interior compartment 4e, a cleaning module lid 4f that closes and seals the upper opening 4b, a water container 4g removably attached to the lower end 4c through a clipping member 4h that is fixedly attached to the sidewall 4d, and at least one cleaning module coupling magnet 4i and a cleaning module guide member 4j both placed on a second upper connecting surface 4k of the cleaning module lid 4f, the water container 4g defines a cavity 4l and is configured to separately store clean water and waste water. A breast interface assembly 5 configured to express breast milk with a breast shield 5a, a vacuum valve 5b, a milk collector 5c and a hose connecting segment 5d, the milk collector 5c is configured to receive expressed breast milk and transfer it to the hose connecting segment 5d. An oral interface assembly 6 configured for milk feeding. And, at least one breast interface assembly hose 7 and an oral interface assembly hose 8, the at least one breast interface assembly hose 7 is removably attached to the hose connecting segment 5d of the breast interface assembly 5 and to the at least one breast interface assembly hose connector 2d of the assembly head 2 when operating the breast interface assembly 5, the oral interface assembly hose 8 is removably attached to the oral interface assembly 6 and to the oral interface assembly hose connector 2e of the assembly head 2 when operating the oral interface assembly 6, the breast interface assembly 5 and the oral interface assembly 6 can be selectively operated simultaneously or independently. Wherein the first upper connecting surface 3f of the milk container lid 3b of the milking module 3 is removably attached to the lower connecting surface 2i of the assembly head 2 through the at least one milking module coupling magnet 3d for operating one or both of the breast interface assembly 5 and the oral interface assembly 6 and selectively controlling the temperature of the expressed breast milk stored in the milk container 3*a* of the milking module 3 simultaneously or independently, the at least one milking module coupling magnet 3*d* further controls the alignment of the two connecting surfaces. Wherein the expressed breast milk is transported from the breast interface assembly 5 to the milk container 3*a* of the milking module 3 when operating the breast interface assembly 5, the expressed breast milk is transported through the at least one breast interface assembly hose 7, the milk inlet tube 2*g* of the assembly head 2 and the milk transfer tube 3*g* of the milking module 3. Wherein the expressed breast milk is transported from the milk container 3*a* of the milking module 3 to the oral interface assembly 6 when operating the oral interface assembly 6, the expressed breast milk is transported through the transfer tube 3*g* of the milking module 3, the milk outlet tube 2*h* of the assembly head 2 and the oral interface assembly hose 8. Wherein the second upper connecting surface 4*k* of the cleaning module lid 4*f* is removably attached to the lower connecting surface 2*i* of the assembly head 2 through the at least one cleaning module coupling magnet 4*i* for cleaning the lactation assembly 1, the at least one cleaning module coupling magnet 4*i* further controls the alignment of the two connecting surfaces. Wherein the breast interface assembly 5 is placed in the interior compartment 4*e* of the body 4*a* of the cleaning module 4 and the oral interface assembly 6 is placed in the cavity 4*l* of the water container 4*g* of the cleaning module 4 when cleaning the lactation assembly 1. Wherein clean water from the water container 4*g* of the cleaning module 4 is circulated through the cleaning module 4 and the assembly head 2 and returns to the water container 4*g* of the cleaning module 4 as waste water when cleaning the lactation assembly 1. Wherein the operations of the lactation assembly 1 are controlled through the touch screen 2*a*. And, wherein data associated with breast milk production, consumption and temperature is stored into the assembly head 2 and can be accessed through the touch screen 2*a*, the lactation assembly 1 uses this data to determine optimum time windows for expressing breast milk and for milk feeding and to determine optimum milk temperature for the infant.

In an embodiment of the present invention, the milking module guide member 3*e* facilitates alignment control of the first upper connecting surface 3*f* of the milk container lid 3*b* of the milking module 3 and the lower connecting surface 2*i* of the assembly head 2.

In another embodiment of the present invention, the cleaning module guide member 4*j* facilitates alignment control of the second upper connecting surface 4*k* of the cleaning module lid 4*f* and the lower connecting surface 2*i* of the assembly head 2.

In another embodiment of the present invention, the user-actuatable control element 2*c* of the assembly head 2 is either a button, a toggle or a switch.

In another embodiment of the present invention, the vacuum valve 5*b* of the breast interface assembly 5 is membrane-actuated.

In another embodiment of the present invention, the oral interface assembly 6 is either a pacifier, a feeding bottle or a nipple assembly.

In another embodiment of the present invention, transparent materials are used to enable viewing the path of the expressed breast milk from the milk container 3*a* of the milking module 3 to the oral interface assembly 6, from the breast shield 5*a* to the at least one breast interface assembly hose connector 2*d*, or both.

In another embodiment of the present invention, the lactation assembly 1, upon detecting cessation of suction by the infant, redirects the expressed breast milk back into the milk container 3*a* of the milking module 3 to prevent drips and preserve expressed breast milk for future use.

In yet another embodiment of the present invention, the lactation assembly 1 has a portable and ergonomic design.

An advantage of the present invention is the ability to perform simultaneous milk extraction, storage, and infant feeding, thereby streamlining lactation workflows, reducing feeding delays, and improving convenience for caregivers.

Another advantage of the present invention is the inclusion of an integrated milk heating system, ensuring that expressed breast milk is delivered at an optimal temperature immediately prior to consumption, enhancing infant comfort and safety.

Another advantage of the present invention is the provision of an automated self-cleaning mechanism, which enhances device hygiene, facilitates ease of maintenance, and permits use in environments where immediate manual cleaning may be impractical.

Another advantage of the present invention is the integration of a data-linked informational interface, capable of monitoring and recording data related to milk production, infant consumption, feeding schedules, and milk temperature, thereby improving feeding management and parental reassurance.

Another advantage of the present invention is the dynamic control of milk inflow and outflow via a touchscreen interface, allowing personalized adjustment of both extraction rates and feeding flow to meet the specific needs of both the mother and the infant.

Another advantage of the present invention is the use of a high-strength magnetic coupling system, which ensures secure, stable, and precise alignment of detachable modules during operation, thereby preventing accidental disconnection.

Another advantage of the present invention is the use of transparent materials, enabling visual monitoring of the expressed milk's path from the milking module to the infant, providing users with added reassurance and operational oversight.

Another advantage of the present invention is the automatic milk return mechanism, which detects cessation of suction by the infant and automatically redirects remaining milk back into the storage container, preventing drips and preserving milk for future use.

Another advantage of the present invention is the provision of configurable, user-actuatable controls and a modular system architecture, facilitating rapid and intuitive interchange between extraction, feeding, and cleaning operations.

Still another advantage of the present invention is its portable, ergonomic, and aesthetically pleasing design, which prioritizes safety, comfort, and convenience for both mothers and infants, thereby enhancing the overall breastfeeding experience.

The embodiments of the lactation assembly for improved functionality herein are exemplary and numerous modifications, combinations, variations, and rearrangements can be readily envisioned to achieve an equivalent result, all of which are intended to be embraced within the scope of the appended claims. Further, nothing in the above-provided discussions of the lactation assembly for improved functionality should be construed as limiting the invention to an embodiment or a combination of embodiments. The scope of the invention is defined by the description, drawings, and claims.

What is claimed is:

1. A lactation assembly for improved functionality, the lactation assembly comprises:
   an assembly head with a touch screen, a suction pump, a user-actuatable control element, an oral interface assembly hose connector, a charging port, a milk inlet tube, and a milk outlet tube, the milk inlet tube and the milk outlet tube extend to a lower connecting surface of the assembly head;
   a milking module with a milk container configured to control the temperature of expressed breast milk contained therein, a milk container lid that closes and seals the milk container through a closure thread, at least one milking module coupling magnet and a milking module guide member both placed on a first upper connecting surface of the milk container lid, and a milk transfer tube that projects from a lower surface of the milk container lid;
   a cleaning module with a body that defines an upper opening, a lower end and a sidewall that collectively define an interior compartment, a cleaning module lid that closes and seals the upper opening, a water container removably attached to the lower end through a clipping member that is fixedly attached to the sidewall, and at least one cleaning module coupling magnet and a cleaning module guide member both placed on a second upper connecting surface of the cleaning module lid, the water container defines a cavity and is configured to separately store clean water and waste water;
   a breast interface assembly configured to express breast milk with a breast shield, a vacuum valve, a milk collector and a hose connecting segment, the milk collector is configured to receive expressed breast milk and transfer it to the hose connecting segment;
   an oral interface assembly configured for milk feeding; and
   at least one breast interface assembly hose and an oral interface assembly hose, the at least one breast interface assembly hose is removably attached to the hose connecting segment of the breast interface assembly and to the at least one breast interface assembly hose connector of the assembly head when operating the breast interface assembly, the oral interface assembly hose is removably attached to the oral interface assembly and to the oral interface assembly hose connector of the assembly head when operating the oral interface assembly, the breast interface assembly and the oral interface assembly can be selectively operated simultaneously or independently;
   wherein the first upper connecting surface of the milk container lid of the milking module is removably attached to the lower connecting surface of the assembly head through the at least one milking module coupling magnet for operating one or both of the breast interface assembly and the oral interface assembly and selectively controlling the temperature of the expressed breast milk stored in the milk container of the milking module simultaneously or independently, the at least one milking module coupling magnet further controls the alignment of the first upper connecting surface of the milk container lid and the lower connecting surface of the assembly head;
   wherein the expressed breast milk is transported from the breast interface assembly to the milk container of the milking module when operating the breast interface assembly, the expressed breast milk is transported through the at least one breast interface assembly hose, the milk inlet tube of the assembly head and the milk transfer tube of the milking module;
   wherein the expressed breast milk is transported from the milk container of the milking module to the oral interface assembly when operating the oral interface assembly, the expressed breast milk is transported through the transfer tube of the milking module, the milk outlet tube of the assembly head and the oral interface assembly hose;
   wherein the second upper connecting surface of the cleaning module lid is removably attached to the lower connecting surface of the assembly head through the at least one cleaning module coupling magnet for cleaning the lactation assembly, the at least one cleaning module coupling magnet further controls the alignment of the second upper connecting surface of the cleaning module lid and the lower connecting surface of the assembly head;
   wherein the breast interface assembly is placed in the interior compartment of the body of the cleaning module and the oral interface assembly is placed in the cavity of the water container of the cleaning module when cleaning the lactation assembly;
   wherein clean water from the water container of the cleaning module is circulated through the cleaning module and the assembly head and returns to the water container of the cleaning module as waste water when cleaning the lactation assembly;
   wherein the operations of the lactation assembly are controlled through the touch screen; and wherein data associated with breast milk production, consumption and temperature is stored into the assembly head and can be accessed through the touch screen, the lactation assembly uses this data to determine optimum time windows for expressing breast milk and for milk feeding and to determine optimum milk temperature for the infant.

2. The lactation assembly for improved functionality of claim 1, wherein the milking module guide member facilitates alignment control of the first upper connecting surface of the milk container lid of the milking module and the lower connecting surface of the assembly head.

3. The lactation assembly for improved functionality of claim 1, wherein the cleaning module guide member facilitates alignment control of the second upper connecting surface of the cleaning module lid and the lower connecting surface of the assembly head.

4. The lactation assembly for improved functionality of claim 1, wherein the user-actuatable control element of the assembly head is either a button, a toggle or a switch.

5. The lactation assembly for improved functionality of claim 1, wherein the vacuum valve of the breast interface assembly is membrane-actuated.

6. The lactation assembly for improved functionality of claim 1, wherein the oral interface assembly is either a pacifier, a feeding bottle or a nipple assembly.

7. The lactation assembly for improved functionality of claim 1, wherein transparent materials are used to enable viewing the path of the expressed breast milk from the milk container of the milking module to the oral interface assembly, from the breast shield to the at least one breast interface assembly hose connector, or both.

8. The lactation assembly for improved functionality of claim 1, wherein the lactation assembly, upon detecting cessation of suction by the infant, redirects the expressed breast milk back into the milk container of the milking module to prevent drips and preserve expressed breast milk for future use.

9. The lactation assembly for improved functionality of claim 1, wherein the lactation assembly has a portable and ergonomic design.

* * * * *